US006896691B2

(12) United States Patent  
Boylan et al.

(10) Patent No.: US 6,896,691 B2  
(45) Date of Patent: May 24, 2005

(54) SYSTEM FOR, AND METHOD OF, BLOCKING THE PASSAGE OF EMBOLI THROUGH A VESSEL

(75) Inventors: John F. Boylan, Murrieta, CA (US); John A. Simpson, Carlsbad, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 526 days.

(21) Appl. No.: 10/175,012

(22) Filed: Jun. 19, 2002

(65) Prior Publication Data

US 2002/0156520 A1 Oct. 24, 2002

Related U.S. Application Data

(62) Division of application No. 09/469,993, filed on Dec. 21, 1999, now Pat. No. 6,443,971.

(51) Int. Cl.[7] .............................................. A61M 29/00
(52) U.S. Cl. ........................................................ 606/200
(58) Field of Search ............................ 606/200, 1, 113, 606/114, 127, 191, 192, 195, 198; 623/1.11

(56) References Cited

U.S. PATENT DOCUMENTS

| 3,952,747 A | 4/1976 | Kimmell, Jr. |
| 4,452,908 A | 6/1984 | Ball et al. |
| 4,494,531 A | 1/1985 | Gianturco |

(Continued)

FOREIGN PATENT DOCUMENTS

| EP | 0 427 429 A2 | 5/1991 |
| EP | 0 472 334 A1 | 2/1992 |
| WO | WO92/03097 | 3/1992 |
| WO | WO96/01591 | 1/1996 |
| WO | WO97/17100 | 5/1997 |
| WO | WO99/16382 | 4/1999 |
| WO | WO99/23976 | 5/1999 |

Primary Examiner—Kevin T. Truong  
(74) Attorney, Agent, or Firm—Fulwider Patton Lee & Utecht, LLP

(57) ABSTRACT

A self-expanding filter has a deployable resilient distal portion with properties of passing fluid (e.g. blood) in a vessel (e.g. an artery) and blocking the passage of emboli in the fluid. The self-expanding filter is disposed in the vessel, in the direction of fluid flow in the vessel, with its resilient proximal and distal ends at positions past a lesion in the vessel. The distal end of the self-expanding filter is then deployed against the vessel wall. An interventional device, such as an expandable member (e.g. balloon) and expandable stent are disposed in the vessel at the position of the lesion in the vessel. The expandable member is then dilated to expand the expandable stent against the vessel wall and open the vessel at the lesion position. Fluid (blood) flows through the deployed distal end of the self-expanding filter and emboli created during the procedure are trapped by the deployed distal end of the filter. The expandable member is then collapsed after all of the emboli have been trapped by the deployed distal end of the self-expanding filter. The resilient proximal end of the self-expanding filter is thereafter deployed against the vessel wall. This causes the emboli to be trapped between the vessel wall and the proximal and distal ends of the self-expanding filter. Alternatively, the expandable member may be deflated and withdrawn from the vessel after the proximal end of the filter has been deployed against the wall of the vessel.

20 Claims, 3 Drawing Sheets

U.S. PATENT DOCUMENTS

| | | | |
|---|---|---|---|
| 4,612,931 | A | 9/1986 | Dormia |
| 4,619,246 | A | 10/1986 | Molgaard-Nielsen et al. |
| 4,643,184 | A | 2/1987 | Mobin-Uddin |
| 4,650,466 | A | 3/1987 | Luther |
| 4,662,885 | A | 5/1987 | DiPisa, Jr. |
| 4,688,553 | A | 8/1987 | Metals |
| 4,706,671 | A | 11/1987 | Weinrib |
| 4,723,549 | A | 2/1988 | Wholey et al. |
| 4,727,873 | A | 3/1988 | Mobin-Uddin |
| 4,781,177 | A | 11/1988 | Lebigot |
| 4,790,812 | A | 12/1988 | Hawkins, Jr. et al. |
| 4,790,813 | A | 12/1988 | Kensey |
| 4,794,928 | A | 1/1989 | Kletschka |
| 4,832,055 | A | 5/1989 | Palestrant |
| 4,873,978 | A | 10/1989 | Ginsburg |
| 4,921,478 | A | 5/1990 | Solano et al. |
| 4,921,484 | A | 5/1990 | Hillstead |
| 4,969,891 | A | 11/1990 | Gewertz |
| 4,990,156 | A | 2/1991 | Lefebvre |
| 4,997,435 | A | 3/1991 | Demeter |
| 4,998,539 | A | 3/1991 | Delsanti |
| 5,053,008 | A | 10/1991 | Bajaj |
| 5,064,428 | A | 11/1991 | Cope et al. |
| 5,071,407 | A | 12/1991 | Termin et al. |
| 5,092,839 | A | 3/1992 | Kipperman |
| 5,100,425 | A | 3/1992 | Fischell et al. |
| 5,102,415 | A | 4/1992 | Guenther et al. |
| 5,108,419 | A | 4/1992 | Reger et al. |
| 5,152,777 | A | 10/1992 | Goldberg et al. |
| 5,160,342 | A | 11/1992 | Reger et al. |
| 5,192,286 | A | 3/1993 | Phan et al. |
| 5,324,304 | A | 6/1994 | Rasmussen |
| 5,329,942 | A | 7/1994 | Gunther et al. |
| 5,330,482 | A | 7/1994 | Gibbs et al. |
| 5,350,398 | A | 9/1994 | Pavcnik et al. |
| 5,370,657 | A | 12/1994 | Irie |
| 5,383,887 | A | 1/1995 | Nadal |
| 5,421,832 | A | 6/1995 | Lefebvre |
| 5,490,859 | A | 2/1996 | Mische et al. |
| 5,496,277 | A | 3/1996 | Termin et al. |
| 5,496,330 | A | 3/1996 | Bates et al. |
| 5,501,694 | A | 3/1996 | Ressemann et al. |
| 5,549,626 | A | 8/1996 | Miller et al. |
| 5,601,595 | A | 2/1997 | Smith |
| 5,626,605 | A | 5/1997 | Irie et al. |
| 5,634,942 | A | 6/1997 | Chevillon et al. |
| 5,649,953 | A | 7/1997 | Lefebvre |
| 5,662,671 | A | 9/1997 | Barbut et al. |
| 5,669,933 | A | 9/1997 | Simon et al. |
| 5,681,347 | A | 10/1997 | Cathcart et al. |
| 5,695,518 | A | 12/1997 | Laerum |
| 5,695,519 | A | 12/1997 | Summers et al. |
| 5,720,764 | A | 2/1998 | Naderlinger |
| 5,725,550 | A | 3/1998 | Nadal |
| 5,733,294 | A | 3/1998 | Forber et al. |
| 5,746,767 | A | 5/1998 | Smith |
| 5,755,790 | A | 5/1998 | Chevillon et al. |
| 5,769,816 | A | 6/1998 | Barbut et al. |
| 5,772,674 | A | 6/1998 | Nakhjavan |
| 5,779,716 | A | 7/1998 | Cano et al. |
| 5,792,145 | A | 8/1998 | Bates et al. |
| 5,792,156 | A | 8/1998 | Perouse |
| 5,792,157 | A | 8/1998 | Mische et al. |
| 5,795,322 | A | 8/1998 | Boudewijn |
| 5,800,457 | A | 9/1998 | Gelbfish |
| 5,800,525 | A | 9/1998 | Bachinski et al. |
| 5,810,874 | A | 9/1998 | Lefebvre |
| 5,814,064 | A | 9/1998 | Daniel et al. |
| 5,827,324 | A | 10/1998 | Cassell et al. |
| 5,833,650 | A | 11/1998 | Imran |
| 5,836,868 | A | 11/1998 | Ressemann et al. |
| 5,846,251 | A | 12/1998 | Hart |
| 5,846,260 | A | 12/1998 | Maahs |
| 5,848,964 | A | 12/1998 | Samuels |
| 5,868,708 | A | 2/1999 | Hart et al. |
| 5,876,367 | A | 3/1999 | Kaganov et al. |
| 5,897,567 | A | 4/1999 | Ressemann et al. |
| 5,910,154 | A | 6/1999 | Tsugita et al. |
| 5,911,734 | A | 6/1999 | Tsugita et al. |
| 5,941,896 | A | 8/1999 | Kerr |
| 5,968,071 | A | 10/1999 | Chevillon et al. |
| 5,976,172 | A | 11/1999 | Homsma et al. |
| 5,980,555 | A | 11/1999 | Barbut et al. |
| 5,989,281 | A | 11/1999 | Barbut et al. |
| 6,001,118 | A | 12/1999 | Daniel et al. |
| 6,013,093 | A | 1/2000 | Nott et al. |
| 6,129,739 | A | 10/2000 | Khosravi |
| 6,179,859 | B1 | 1/2001 | Bates et al. |
| 6,582,448 | B1 * | 6/2003 | Boyle et al. .................. 606/200 |
| 6,758,855 | B2 * | 7/2004 | Fulton et al. ................ 606/200 |

\* cited by examiner

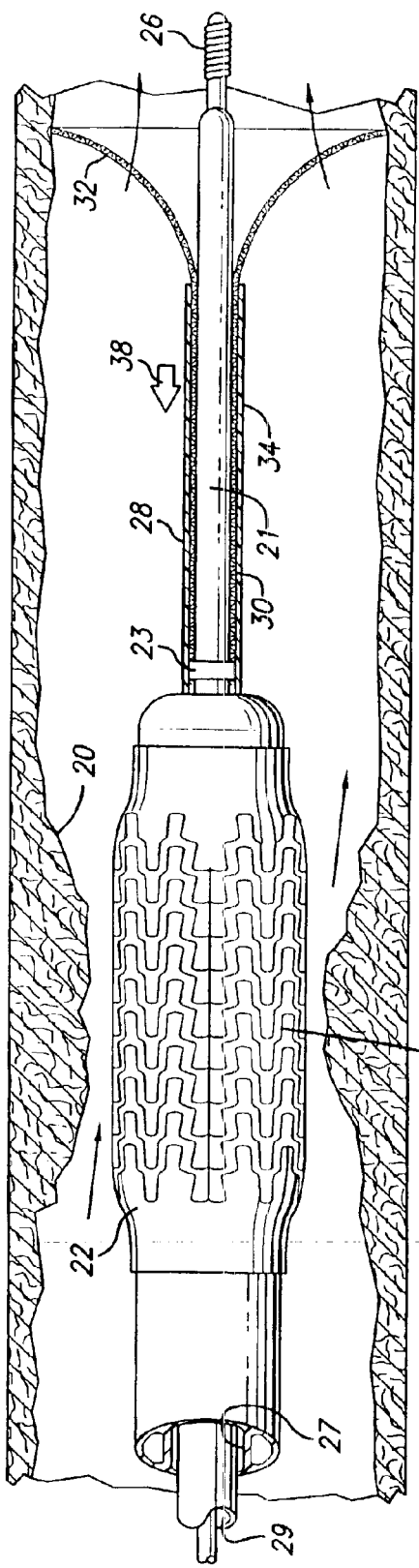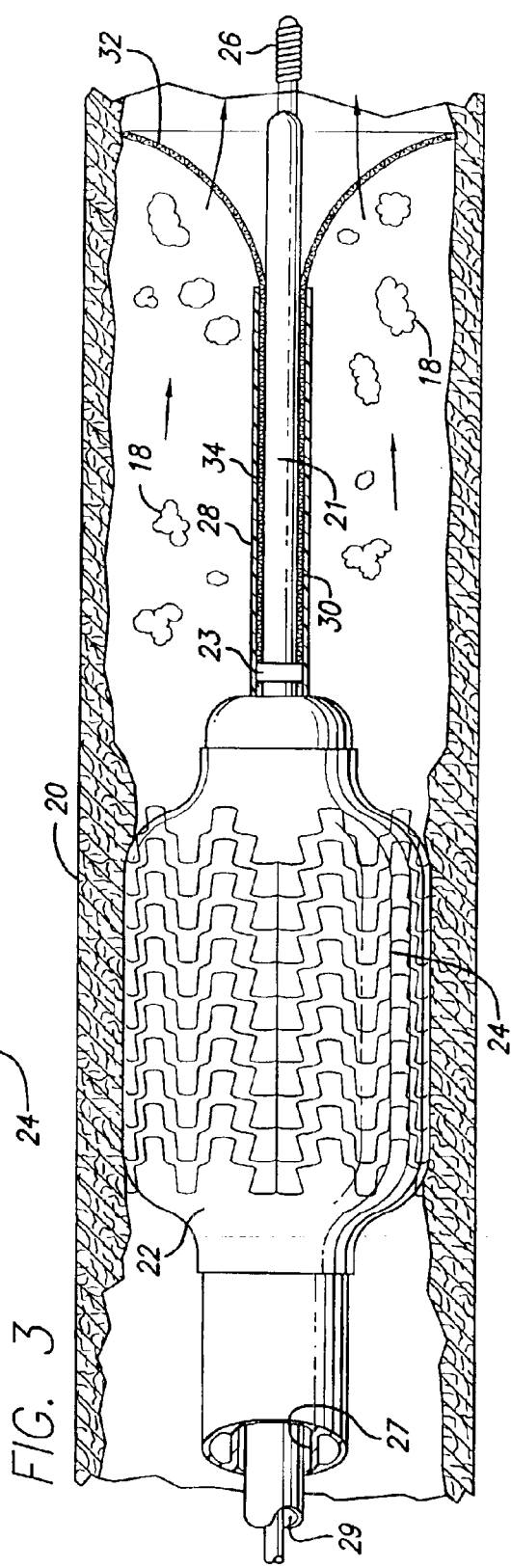

SYSTEM FOR, AND METHOD OF, BLOCKING THE PASSAGE OF EMBOLI THROUGH A VESSEL

CROSS-REFERENCE TO RELATED APPLICATIONS

This is a divisional application of a parent application having U.S. Ser. No. 09/469,933 filed Dec. 21, 1999, now U.S. Pat. No. 6,443,971 whose contents are hereby incorporated by reference.

BACKGROUND OF THE INVENTION

This invention relates to a system for, and a method of, treating occluded vessels (e.g. an artery) and capturing friable emboli which may break away from the lesion in the vessel during an interventional procedure. The system and method of the present invention are especially useful when performing carotid interventional procedures in order to prevent embolic debris from entering and occluding downstream blood vessels leading to the brain which, if blocked, may cause a stroke. However, the system and method of this invention can be adapted by a person of ordinary skill in the art for use in numerous other vascular interventional procedures.

In recent years, numerous procedures have been adapted for expanding blood vessels (e.g. arteries), at the positions of lesions in the blood vessels, so that blood can flow through the blood vessels without obstruction from the lesions. In the process of expanding such blood vessels at the positions of the lesions, emboli may become detached from the lesions and enter the bloodstream and subsequently migrate through the patient's vasculature to block blood vessels leading to sensitive organs such as the brain, where they may induce trauma.

Procedures have been adapted in recent years for preventing embolic debris from flowing through the vessels in the direction of the blood flow. For example, filters have been provided for trapping the emboli. When lesions develop in the carotid artery of a patient, the placement of a filter in the patient's vasculature can somewhat reduce the movement of the emboli to the patient's brain thereby preventing strokes from occurring.

Such filters are usually delivered in a collapsed position through the patient's vasculature and are then expanded once in place to trap the emboli. After emboli have been trapped, the filter is collapsed to remove the filter (with the trapped emboli) from the vessel. However, it is possible for some of the trapped emboli to escape from the filter during the time that the filter is being collapsed and/or removed from the blood vessel. When an interventional procedure is being performed in a carotid artery, even a trace release of emboli can be damaging. For these reasons, attempts to treat lesions in the carotid arteries have been somewhat limited due to the danger presented if all of the embolic debris is not collected during the procedure.

Therefore, in light of the above, it would be desirable to have a system and method which can be utilized to treat an occluded vessel and trap emboli that may be formed during the vascular procedure. Such a system and method also must prevent the emboli from escaping from the filter during the time that the vascular procedure is being performed. Additionally, it also would be advantageous if the filter could remain implanted within the patient's vasculature, thereby eliminating a potential source for the release of trapped emboli since the filter would not have to be collapsed and removed from the blood vessel. Such a device or method should be easy to use and have minimal or no adverse impact on the patient.

SUMMARY OF THE INVENTION

The present invention provides a self-expanding filter having a deployable resilient distal portion with properties of passing fluid (e.g. blood) in a vessel (e.g. an artery) while blocking the passage of emboli released in the fluid. The self-expanding filter is to be disposed within the vessel, in the direction of fluid flow in the vessel, with its resilient proximal and distal ends at positions past the lesion to be treated in the vessel. The distal end of the self-expanding filter is first deployed against the vessel wall, ready to trap any emboli which-may be released into the blood stream. A restraining sheath previously has been placed over the self-expanding filter to maintain the filter in a collapsed position. When the distal end of the filter is to be deployed within the vessel, the physician merely retracts the proximal end of the restraining sheath the proper distance to expose only the distal portion of the filter. Since the filter is self-expanding, the distal end expands and contacts the wall of the vessel to form a seal which prevents emboli from escaping. Blood is permitted to pass through the fine openings of the filter while emboli of particular size are trapped by the filter.

An interventional medical device can be placed in the area of the lesion to treat the lesion and expand the vessel. For example, an expandable member (e.g. dilatation balloon) and expandable stent can be positioned within the vessel at the site of the lesion. The expandable member is dilated to expand the stent against the vessel wall and to open the vessel at the lesion position. The expandable stent also deploys and holds this portion of the vessel open. Any embolic debris created during the interventional procedure will be captured and retained by the self-expanding filter distal to the interventional site and will be prevented from traveling to downstream vessels where possible blockage can occur.

After the interventional procedure has been completed and all of the emboli have been trapped by the filter, the expandable member at the lesion site can then be deflated and withdrawn from the vessel. The remaining portion of the self-expanding filter can thereafter be fully deployed against the vessel wall. This deployment of the filter causes the emboli to be trapped between the vessel wall and the self-expanding filter. The physician fully deploys the remaining portion of the expandable filter by retracting the proximal end of the restraining sheath until the expandable filter is fully unsheathed.

Alternatively, the expandable member may be deflated and withdrawn from the vessel after the proximal end of the self-expanding filter has been deployed against the wall of the vessel to trap the emboli.

The self-expanding filter may be made from a self-expanding stent having a strut pattern which provides an adequate filtering media that can safely and effectively trap emboli of a given size. Alternatively, the self-expanding filter may be made from a filtering material which traps the emboli, but permits blood flow there through. Expandable members, such as self-expanding cylindrical rings, could be placed along the length of the filtering material to create a cylindrical shape filter which will be expandable and able to trap embolic debris. Since the self-expanding filter can be made from biocompatible material, the filter may remain permanently implanted within the patient's vasculature to prevent any trapped emboli from being released into the blood stream.

These and other advantages of the present invention will become more apparent from the following detailed description of the invention, when taken in conjunction with the accompanying exemplary drawings.

BRIEF DESCRIPTION OF THE DRAWINGS

FIG. 2 is an enlarged fragmentary view, partially in section, of the system of FIG. 1 showing the distal end of the filter deployed against the vessel wall at a position past the lesion in the direction of fluid flow.

FIG. 3 is an enlarged fragmentary view, partially in section, of the system of FIGS. 1 and 2 showing the expandable member dilated and the expandable stent expanded against the vessel wall at the position of the lesion.

DETAILED DESCRIPTION OF THE PREFERRED EMBODIMENTS

Figure 1:
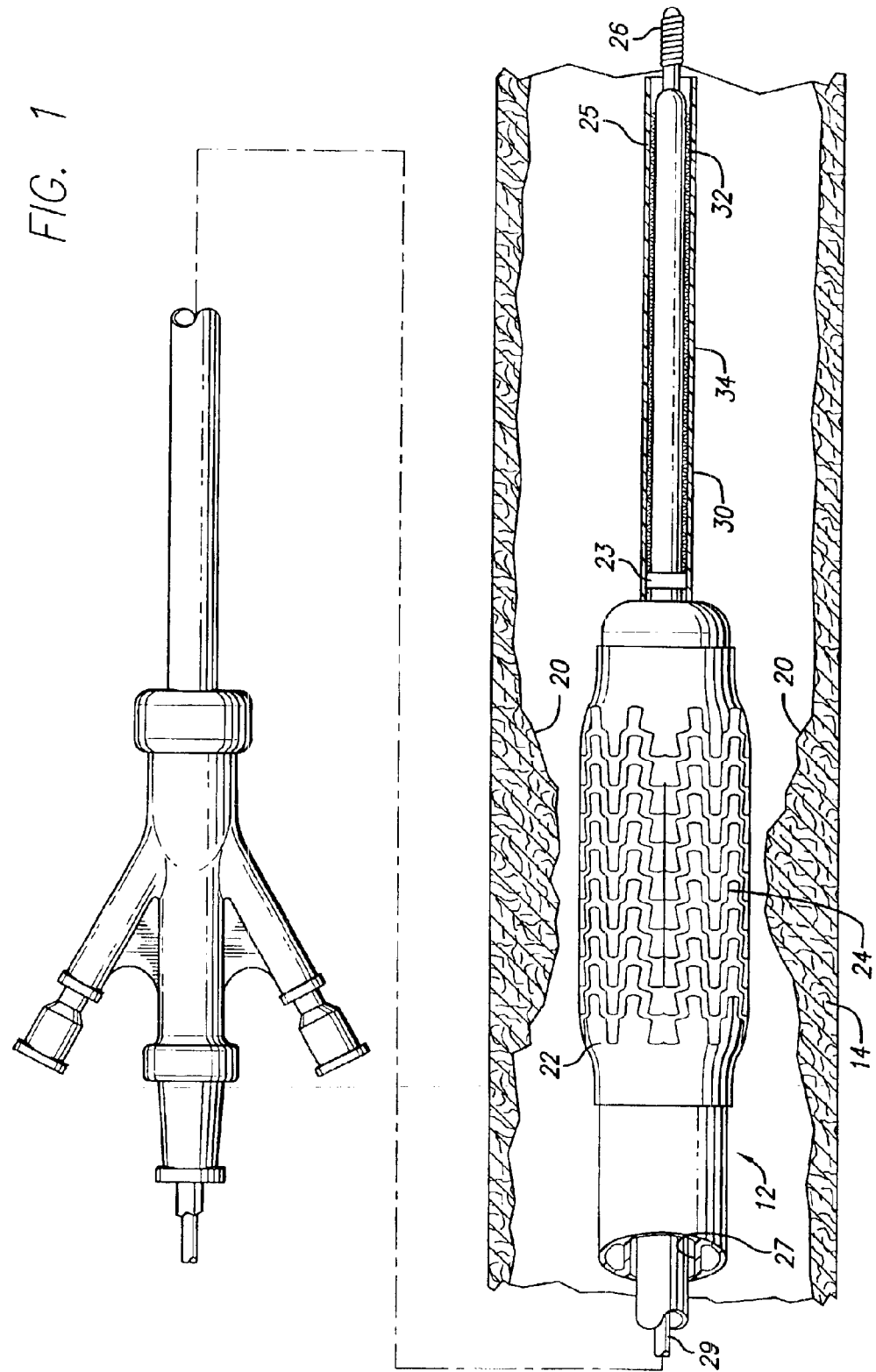
FIG. 1 is a schematic elevational view, partially in section, of a system including a catheter, an expandable member (e.g. a balloon) disposed in a vessel (e.g. an artery) at the position of a lesion in the vessel, an expanding stent disposed on the expandable member and a self-expandable filter disposed on a guide wire at a position past the lesion in the direction of the fluid flow in the vessel.
Figure 4:
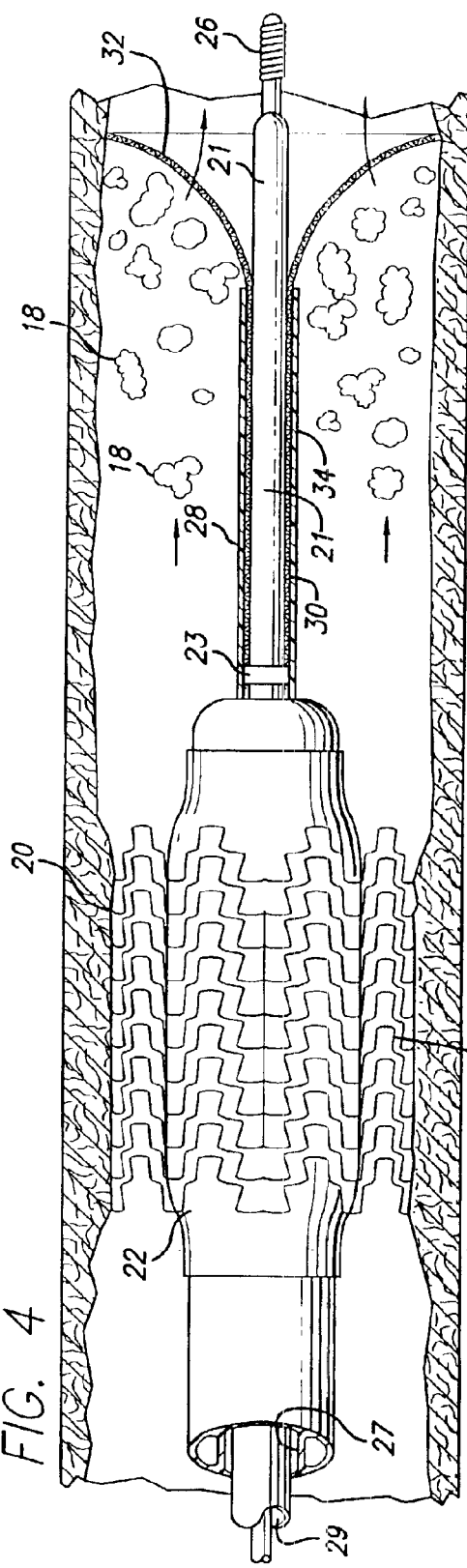
FIG. 4 is an enlarged fragmentary elevational view, partially in section, of the system of FIGS. 1–3 showing the distal end of the self-expanding filter deployed against the vessel wall at the position distal to the lesion and schematically showing the movement of the emboli from the lesion to the deployed distal end of the filter.
Figure 5:
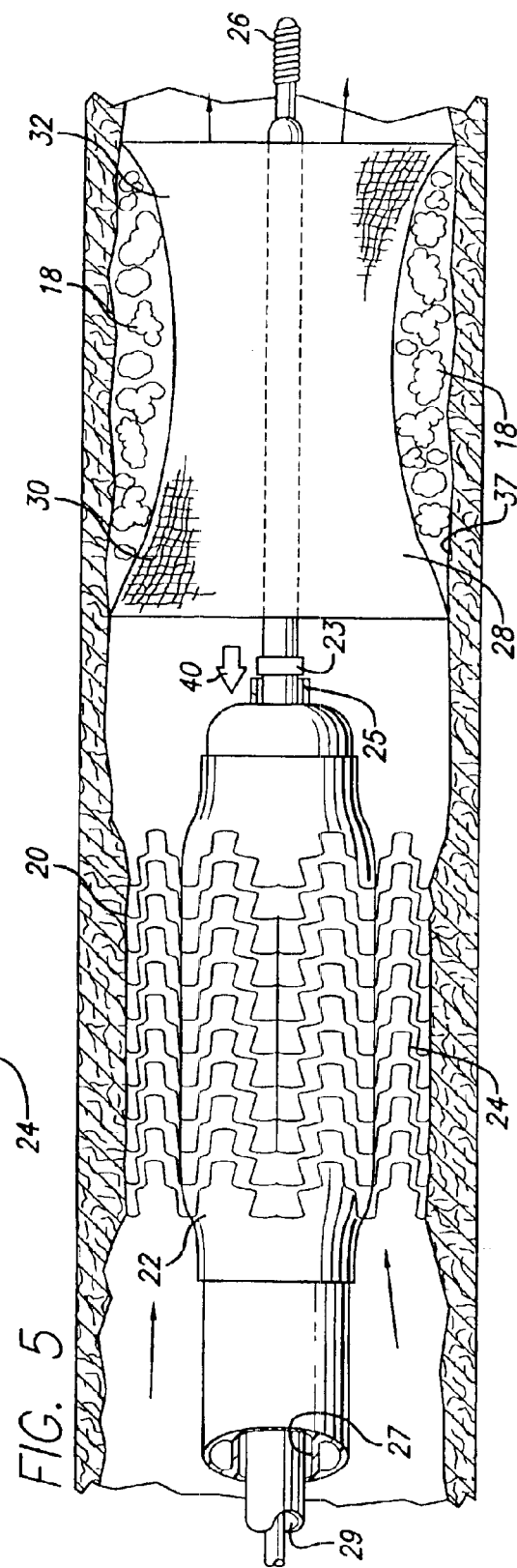
FIG. 5 is a fragmentary elevational view, partially in section, of the system of in FIGS. 1–4 showing the self-expanding filter fully deployed to trap any emboli debris between the filter and the vessel wall.

A preferred embodiment of a system, generally indicated at 10, is shown in FIGS. 1–5 of the drawings. The system 10 includes a catheter 12 which is constructed to extend through a vessel 14, such as a patient's artery.

The system 10 is adapted to be disposed in the vessel 14 (e.g. artery) to pass the fluid (e.g. blood) in the vessel and to block emboli 18 in the blood. The emboli 18 may be produced during the interventional procedure as a lesion 20 is being expanded to open up the vessel 14. The trapping of the emboli 18 from flowing through the vessel 14 prevents the emboli from possibly occluding smaller diameter blood vessels located downstream from the treatment site, which, if the procedure is being performed in the carotid artery, can possibly cause the patient to suffer a stroke.

An expandable member (e.g. balloon) 22 is disposed on the catheter 12 and a stent 24 is suitably mounted on the expandable member. The expandable member 22 and the stent 24 may be constructed in a manner well known in the art. The expandable member 22 and the stent 24 may be disposed at the position of the lesion 20 as shown schematically in FIGS. 1 and 2. When the expandable member 22 is thereafter dilated, it expands the stent 22 against the vessel 14 to open up the vessel. This is shown schematically in FIG. 3. The opening in the vessel 14 is maintained by the stent 24 even after the expandable member 22 is deflated and is thereafter withdrawn in the vessel from the position of the lesion 20.

A self-expanding filter generally indicated at 28 is adapted to be disposed in the vessel. The filter 28 has a resilient proximal portion 30 and a resilient distal portion 32, each of which has properties of passing the fluid in the vessel 14 while blocking the emboli in the fluid. The filter 28 is disposed in the vessel 14 at a position distal to the lesion 20 in the direction of the fluid flow in the vessel. A guide wire 26 may be used to deliver the filter 28 to the position past the lesion 20 in the direction of the fluid flow. The filter 28 is initially constrained within a restraining sheath 34 (FIG. 1) so that the filter 28 can be easily inserted into the vessel to the position past the lesion 20 in the direction of the fluid flow.

The self-expanding filter 28 is placed on a filter holder 21 which, as is shown in FIGS. 1–5, is an elongated tubular member having a distal end and a proximal end (not shown) located outside of the patient. The restraining sheath 34 likewise has a distal end 25 and a proximal end (not shown) located outside of the patient. This restraining sheath 34 is slidable over the filter holder 21 in a coaxial arrangement so that the physician merely has to move the proximal ends of the filter holder 21 and restraining sheath 34 in order to retract the distal end 25 of the restraining sheath the needed length to deploy the self-expanding filter 28. Both the filter holder 21 and the restraining sheath 34 are movable within a lumen 27 formed on the catheter 12. It should be appreciated that a simple mechanism could be attached to the proximal ends of the filter holder 21 and restraining sheath 34 to maintain the restraining sheath 34 at the desired location relative to the filter 28 during usage. Such a mechanism would prevent the sheath 34 from accidentally moving which could cause the entire filter 28 to deploy prematurely. Additionally, the filter holder 21 may include a fitting 23 located proximal to the filter 28 to provide a shoulder element which allows the proximal end of the filter to abut against when the restraining sheath 34 is being retracted. Such a fitting helps to prevent the filter from moving back with the restraining sheath 34 as it is being retracted. This fitting may be a radiopaque marker which also may assist the physician in visualizing the location of the filter when deploying the device in the patient's vasculature.

The filter 28 is initially moved in the vessel 14 to the position distal to the lesion 20 using over-the-wire-techniques. The filter holder 21 includes an internal lumen 29 which receives the guide wire 26. This guide wire 26 is initially positioned in the vessel 14 with the filter 28 being delivered to the area of treatment using over-the-wire techniques. The distal portion 32 of the filter device is then deployed as shown in FIG. 2. The deployment of the resilient distal portion 32 of the filter 28 is provided by moving the restraining sheath 34 relative to the filter holder 21. This is indicated by a hollow arrow 38 in FIG. 2. When deployed in the vessel 24, the distal portion 32 engages the wall of the vessel and prevents emboli from flowing past the filter 28. However, fluid is able to flow through the distal portion 32 of the filter 28.

The catheter 12 including expandable member 22 and the stent 24 can then be disposed in the vessel 14 at the position of the lesion 20 using over-the-wire techniques. In this manner, the restraining sheath/filter holder can be used as a guide wire to position the catheter 12 in position. The expandable member 22 can then be dilated. This causes the stent 24 to expand against the wall of the vessel 14 and expand the vessel 14 at the position of the lesion 20. This is shown schematically in FIG. 3. When the vessel 14 is expanded at the position of the lesion 20, any emboli 18 produced, as shown in FIG. 3, are prevented from passing through the vessel 14 by the deployment of the distal portion 32 of the filter 28 against the wall of the vessel 14.

When all of the emboli 18 created as a result of the interventional procedure are captured by the distal portion 32 of the filter 28, the expandable member 22 can be collapsed and removed from the vessel 14 by moving the catheter 12 out of the vessel. The stent 24 remains in the vessel 14 at the position of the lesion 20 to maintain the vessel open at the position of the lesion.

After the expandable member 22 has been removed from the vessel 14, the restraining sheath 34 is again moved relative to the filter holder 21 to deploy the remaining portion of the filter 28 against the wall of the vessel 14. This is shown schematically in FIG. 5. The movement of the restraining sheath 34 relative to the filter 28 is indicated by a hollow arrow 40 in FIG. 5. The proximal portion 30 of the filter 28 also is constructed to pass fluid and to block the passage of the emboli 18. The emboli 18 are accordingly retained in a pocket 37 defined by the filter 28 and the wall of the vessel 14.

The system 10 may be used in conjunction with current compatible devices. For example, the system 10 may be used in conjunction with balloon dilatation catheters, stent delivery systems, ultrasonic and laser angioplasty devices and atherectomy catheters, and other medical devices. The system 10 will preferably be used during vascular intervention, in particular, carotid artery angioplasty and stenting (i.e. pre-dilation, stenting, post-dilation), however, it can also be used in any procedures in which potential release of emboli debris poses a problem.

The self-expandable filter 28 shown in the embodiments of FIGS. 1–5 is a stent device which has a strut pattern having sufficient porosity to allow blood to flow through the struts of the stent but having small openings to prevent emboli of a particular size from passing therethrough. The self-expandable filter 28 could also be manufactured utilizing a filtering material such as Gortex® manufactured by W. L. Gore & Associates, Inc., or nylon, porous PTFE, Dacron®, or similar material. This filtering material would have a number of self-expanding cylindrical rings attached to it to form a composite cylindrically-shaped filter. The self-expanding cylindrical rings could be made from a material such as Nitinol or other self-expanding materials which will allow the rings to be initially collapsed to a small profile onto the filter holder 21. The restraining sheath will maintain each ring in the collapsed position. Once the restraining sheath is removed, each collapsed ring will move into its fully expanded position and contact the vessel wall. Other embodiments of a self-expandable filter 28 can also be made using other designs and techniques. Additionally, other suitable means for delivering the self-expanding filter 28 to the area of treatment also can be utilized in conjunction with the present invention.

The filter holder 21 can be made from a material such as cross-linked HDPE or other similar materials. The restraining sheath 34 can be made from a material such as polyolifin. A material such as polyolifin can be used since it has sufficient strength to hold the compressed filter and has relatively low frictional characteristics to minimize any friction between the filter 28 and the sheath 34. Friction can be further reduced by applying a coat of lubricant, such as Dow 360 or Microglide®, to the inside surface of the restraining sheath 34 before the filter 28 is loaded onto the filter holder 21. Alternatively, the distal most portion of the restraining sheath 34 could be made from polyolefin, or similar material, and the remaining portion of the sheath could be made from a different material to provide added strength to the sheath.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

What is claimed:

1. A method of expanding a lesion in a body vessel and passing a fluid in the vessel while blocking the passage of emboli in the fluid through the vessel, comprising the steps of:

providing an expandable member;

providing a filter having partially deployable and fully deployable positions;

delivering the expandable member in the vessel at the position of the lesion and deploying the filter in the vessel at a position past the lesion in the direction of the fluid flow;

partially deploying the filter against the wall of the vessel;

thereafter expanding the expandable member against the lesion to expand the vessel at the position of the lesion; and fully deploying the filter against the wall of the vessel to pin emboli against the wall of the vessel.

2. The method as set forth in claim 1, wherein:

the filter is constrainable and is deployable from its constrainable position and the filter is constrained during the movement of the filter in the vessel to the position past the lesion.

3. The method as set forth in claim 2, wherein:

the filter has resilient proximal and distal ends which are constrainable from deployment against the wall of the vessel and which are deployable to positions against the wall of the vessel when the constraints on the proximal and distal ends are released; and a constraint is provided on the resilient proximal and distal ends of the filter to provide for an initial release of the constraint on the resilient distal end of the filter and a subsequent release of the constraint on the resilient proximal end of the filter.

4. The method as set forth in claim 3, wherein:

the constraint on the resilient distal end of the filter is initially released to provide for a deployment of the resilient distal end of the filter against the wall of the vessel; and the constraint on the resilient proximal end of the filter is thereafter released to provide for a deployment of the resilient proximal end of the filter against the wall of the vessel.

5. The method as set forth in claim 1, wherein:

the filter has deployable resilient proximal and distal ends;

the resilient proximal and distal ends of the filter are constrainable to positions displaced from the wall of the filter;

the filter is disposed within a restraining sheath during the movement of the filter to the position past the lesion; and the restraining sheath is movable relative to the filter to initially release the constraint on the resilient distal end of the filter and to subsequently release the constraint on the resilient proximal end of the filter.

6. A method for expanding a lesion in a body vessel and passing the fluid in the vessel while blocking the passage of emboli in the fluid through the vessel, comprising the steps of:

providing an interventional device for performing an interventional procedure in the body vessel;

providing a filter having partially deployable and fully deployable positions;

delivering the interventional device in the vessel at the position of the lesion;

deploying the filter into die vessel at a position past the lesion in the direction of the fluid flow partially deploying the filter against the wail of the vessel;

treating the lesion with the interventional device; and fully deploying the filter against the wall of the vessel to trap any emboli between the filter and the wall of the vessel.

7. The method of claim 6, wherein:

the interventional device comprises a self-expanding stent and a stent delivery catheter.

8. The method of claim 6, wherein:

the interventional device comprises a balloon-expandable stent and a stent delivery catheter.

9. A method for providing a system for expanding a vessel at a lesion in the vessel, passing a fluid in the expanded vessel, and blocking the passage through the vessel of emboli in the fluid, comprising:

providing an expandable member constructed for disposition at the lesion in the vessel;

disposing a stent on the expandable member for expansion against the vessel when the expandable member is expanded at the lesion;

providing a self-expanding filter constructed for disposition in the vessel distal to the lesion in the direction of the fluid flow;

deploying the stein against the wall of the vessel to pass the fluid;

partially deploying the filler to block the passage of emboli released into the vessel; and fully deploying the filter against the wall of the vessel to create a trapping pocket with the wall of the vessel for retaining trapped emboli against the wall of the vessel.

10. A method for providing a system for blocking the passage of emboli in fluid flowing through a vessel, comprising:

providing an elongate member;

providing a sheath slidably disposed on the elongate member;

providing a self-expanding filter contained between the sheath and the elongate member;

partially retracting the sheath;

partially deploying the self-expanding filter against the wall of the vessel to pass the fluid and to block the passage of emboli in the vessel;

fully retracting the sheath to release the self-expanding filter; and fully deploying the self-expanding filler against the wall of the vessel to trap the emboli between the filter and the wall of the vessel.

11. The method of claim 10, wherein the elongate member further includes a shoulder located proximally to the filter, wherein the shoulder prevents proximal movement of the filter when the sheath is retracted.

12. The method of claim 10, wherein the self-expanding filter includes a resilient proximal portion and a resilient distal portion, and a filtering material attached to the resilient proximal portion and to the resilient distal portion, wherein the proximal portion does not contact the vessel wall when the self-expanding filter is partially deployed and the distal portion and the proximal portion contact the vessel wall when the self-expanding filter is fully deployed.

13. The method of claim 10, wherein the self-expanding filler includes a filtering material and a plurality of self-expanding rings attached to the filtering material so as to form a generally cylindrical shape when the self-expanding filter is fully deployed.

14. The method of claim 10, wherein the self-expanding filter includes a stent device having small openings to prevent the emboli from passing therethrough.

15. The method of claim 10, further comprising:

providing a catheter having an expandable member and a lumen;

disposing a stent on the expandable member; and dimensioning the sheath and the elongate member so as to be movable through the lumen of the catheter.

16. A method for providing a system for expanding a vessel at a lesion in the vessel and for blocking the passage of emboli in the fluid flowing through the vessel, comprising:

providing a catheter having an expandable member and a lumen;

disposing a stern on the expandable member;

providing an elongate member that is dimensioned to be movable through the lumen of the catheter;

slidably disposing a sheath on the elongate member;

holding a filter between the sheath and the elongate member;

partially retracting the sheath;

partially deploying the filter against the wall of the vessel to pass the fluid and to block the passage of emboli in the vessel;

fully retracting the sheath to release the filter; and fully deploying the filter against the wall of the vessel to trap the emboli between the filter and the wall of the vessel.

17. The method at claim 10, wherein the elongate member further includes a shoulder located proximally to the filter, wherein the shoulder prevents proximal movement of the filter when the sheath is retracted.

18. The method of claim 10, wherein the filter includes a resilient proximal portion and a resilient distal portion, and a filtering material attached to the resilient proximal portion and to the resilient distal portion, wherein the proximal port ion does not contact the proximal portion contact the vessel wall when the self-expanding filter is fully deployed.

19. The method of claim 10, wherein the filter includes a filtering material and a plurality of self-expanding rings attached to the filtering material so as to form a generally cylindrical shape when the filter is fully deployed.

20. The method of claim 16, wherein the self-expanding filter includes a stent device hiving small openings to prevent the emboli from passing therethrough.

* * * * *

UNITED STATES PATENT AND TRADEMARK OFFICE
CERTIFICATE OF CORRECTION

PATENT NO. : 6,896,691 B2
DATED : May 24, 2005
INVENTOR(S) : John F. Boylan and John A. Simpson It is certified that error appears in the above-identified patent and that said Letters Patent is hereby corrected as shown below:

Column 6,
Line 11, delete "filly" and insert instead -- fully --.
Line 51, delete "arc" and insert instead -- are --.

Column 7,
Line 5, delete "die" and insert instead -- the --.
Line 32, delete "stein" and insert instead -- stent --.

Column 8,
Line 29, delete "stern" and insert instead -- stent --.
Lines 45, 49 and 55, delete "10" and insert instead -- 16 --.
Line 60, delete "hiving" and insert instead -- having --.

Signed and Sealed this

Twenty-third Day of August, 2005

JON W. DUDAS
*Director of the United States Patent and Trademark Office*